United States Patent [19]

Lunnen et al.

[11] Patent Number: 5,030,569

[45] Date of Patent: Jul. 9, 1991

[54] METHOD FOR PRODUCING THE AFL II RESTRICTION ENDONUCLEASE AND METHYLASE

[75] Inventors: Keith D. Lunnen, Newbury; Geoffrey G. Wilson, Boxford, both of Mass.

[73] Assignee: New England Biolabs, Inc., Beverly, Mass.

[21] Appl. No.: 440,438

[22] Filed: Nov. 20, 1989

Related U.S. Application Data

[63] Continuation of Ser. No. 109,056, Oct. 15, 1987, abandoned.

[51] Int. Cl.$^5$ .................. C12N 15/52; C12N 9/22; C12N 1/21
[52] U.S. Cl. .................. 435/172.3; 435/199; 435/252.33; 435/320.1; 536/27; 935/29; 935/73; 935/80
[58] Field of Search ............... 435/199, 172.3, 320, 435/252.3; 536/27; 935/29, 73, 80, 82

[56] References Cited

PUBLICATIONS

Greene, P. J. et al. (1981) J. Biol. Chem. 256(5); 2143–2153.
Newman, A. K. et al. (1981) J. Biol. Chem. 256(5); 2131–2139.
Schoner, B. et al. (1983) Gene 24; 227–235.
Walder, R. Y. et al. (1984) J. Biol. Chem. 259(12); 8015–8026.
Lunnen, K. D. et al. (1988) Gene 74; 25–32.
Wilson, G. G. (1988) Trends in Genetics 4; 314–318.
Wilson, G. G. (1988) Gene 74; 281–289.
Borck, K. et al. (1976) Molec Gen. Genet. 146; 199–207.
Kosykh et al., Molec. gen. Genet. 178:717–718 (1980).
Mann et al., Gene 3:97–112 (1978).
Walder et al., Proc. Nat. Acad. Sci. USA 78:1503–1507 (1981).
Bougueleret et al., Nucleic Acids Res. 12: 3659–3676 (1984).
Gingeras and Brooks, Proc. Natl. Acad. Sci. USA 80:402–406 (1983).
Theriault and Roy, Gene 19:355–359, (1982).
Blumenthal et al., J. Bacteriol. 164:501–509 (1985).
Kiss et al., Nucleic Acids Res. 13:6403–6421 (1985).
Szomolanyi et al., Gene 10:219–225 (1980).
Janulaitis et al., Gene 20:197–204 (1982).
Kiss and Baldauf, Gene 21:111–119 (1983).
Walder et al., J. Biol. Chem. 258:1235–1241 (1983).
Raleigh and Wilson, Proc. Natl. Acad. Sci. USA 83:9070–9074 (1986).
Whitehead, P. R. and Brown N. L.; J. Gen. Microbiol. 131:951–958 (1985).
Birnboin and Doly, Nucleic Acids Res. 7:1513 (1979).

Primary Examiner—Elizabeth C. Weimar
Assistant Examiner—Charles L. Patterson, Jr.
Attorney, Agent, or Firm—Gregory D. Williams; David G. Conlin

[57] ABSTRACT

The present invention is directed to a method for cloning and producing the Afl II restriction endonuclease by 1) introducing the restriction endonuclease gene from Anabaena flos-aquae into a host whereby the restriction gene is expressed; 2) fermenting the host which contains the plasmid encoding and expressing the Afl II restriction endonuclease activity, and 3) purifying the Afl II restriction endonuclease from the fermented host which contains the plasmid encoding and expressing the Afl II restriction endonuclease activity.

11 Claims, 3 Drawing Sheets

RESTRICTION MAP OF 12.4Kb XhoII INSERT ENCODING AfIII RESTRICTION ENDONUCLEASE AND METHYLASE

Determination of Afl II restriction endonuclease activity in the crude extracts E. coli carrying the plasmid pKLAflIIRM-520-4

METHOD FOR PRODUCING THE AFL II RESTRICTION ENDONUCLEASE AND METHYLASE

This is a continuation of copending application Ser. No. 07/109,056 filed on Oct. 15, 1987, abandoned.

BACKGROUND OF THE INVENTION

The present invention relates to clones for the Afl II restriction endonuclease and modification methylase, and the production of the enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Close to one hundred different restriction endonucleases have been identified among the many hundreds of bacterial species that have been examined to date.

Bacteria tend to possess at most only a small number restriction endonucleases per species. The endonucleases typically are named according to the bacteria from which they are derived. Thus, the species *Haemophilus aegyptius*, for example synthesizes 3 different restriction endonucleases, named Hae I, Hae II and Hae III. Those enzymes recognize and cleave the sequences (AT)GGCC(AT),PuGCGCPy and GGCC respectively. *Escherichia coli* RY13, on the other hand, synthesizes only one enzyme, EcoR I, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The breakup that takes place disables many of the infecting genes and renders the DNA susceptible to further degradation by non-specific endonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA . that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (Eco RII: Kosykh et al., Molec. gen. Genet 178: 717-719, (1980); HhaII: Mann et al., Gene 3: 97-112, (1978); PstI: Walder et al., Proc. Nat. Acad. Sci. 78 1503-1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival. Another cloning approach involves transferring systems initially characterized as plasmid-borne into *E. coli* cloning plasmids (EcoRV: Bougueleret et al., Nucl. Acid. Res. 12:3659-3676, 1984; PaeR7: Gingeras and Brooks, Proc. Natl. Acad. Sci. USA 80:402-406, 1983; Theriault and Roy, Gene 19:355-359 1982; PvuII: Blumenthal et al., J. Bacteriol. 164:501-509, 1985). Finally, a growing number of systems are now being cloned by selection for an active methylase gene referring to our Patent application No.: 707079 (BsuRI: Kiss et al., Nucl. Acid. Res. 13:6403-6421, 1985). Since restriction and modification genes are often closely linked, both genes can often be cloned simultaneously. This selection does not always yield a complete restriction system however, but instead yields only the methylase gene (BspRI: Szomolanyi et al., Gene 10:219-225, (1980); Bcn I: Janulaitis et al, Gene 20: 197-204 (1982); Bsu RI: Kiss and Baldauf, Gene 21: 111-119, (1983); and Msp I: Walder et al., J. Biol. Chem. 258:1235-1241, (1983)).

In some systems the cloning problem may lie in trying to introduce the endonuclease gene into a host not already protected by modification. If the methylase gene and endonuclease gene are introduced on a common DNA fragment, the methylase gene must modify or protect the host before the endonuclease gene cleaves the host's genome.

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, Proc. Natl. Acad. Sci., USA 83:9070-9074, 1986). Therefore, it is also necessary to carefully consider which E. coli strain(s) to use for cloning.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the Afl II restriction endonuclease and modification methylase derived from *Anabaena flos-aquae*, as well as related methods for the production of the enzymes. More specifically, this invention relates to clones which express the restriction endonuclease Afl II, an enzyme which recognizes the DNA sequence CTTAAG and cleaves between the C and T residue. See Whitehead, P. R. and Brown N. L., 1985, J. Gen. Microbiol. 131:951-958, the disclosure of which is hereby incorporated by reference herein. Afl II restriction endonuclease produced in accordance with the present invention is substantially pure and free of the contaminants normally found in Afl II preparations made by conventional techniques, such as that disclosed by Whitehead & Brown, supra.

The preferred method for cloning this enzyme comprises forming a library containing the DNA from *Anabaena flos-aquae*, isolating those clones which contain DNA coding for the Afl II modification methylase and screening these to identify those that also contain the Afl II restriction endonuclease gene.

DETAILED DESCRIPTION OF THE INVENTION

The present invention relates to clones of the Afl II restriction and modification genes, as well to the restriction endonuclease Afl II produced from such clones. The Afl II genes are cloned by a method which takes advantage of the fact that certain clones which are selected on the basis of containing and expressing the Afl II modification or methylase gene also contain the Afl II restriction gene. The DNA of such clones is resistant to digestion, in vitro, by the Afl II restriction endonuclease. This resistance to digestion affords a means for selectively isolating clones encoding the Afl II methylase and restriction endonuclease.

Figure 1:
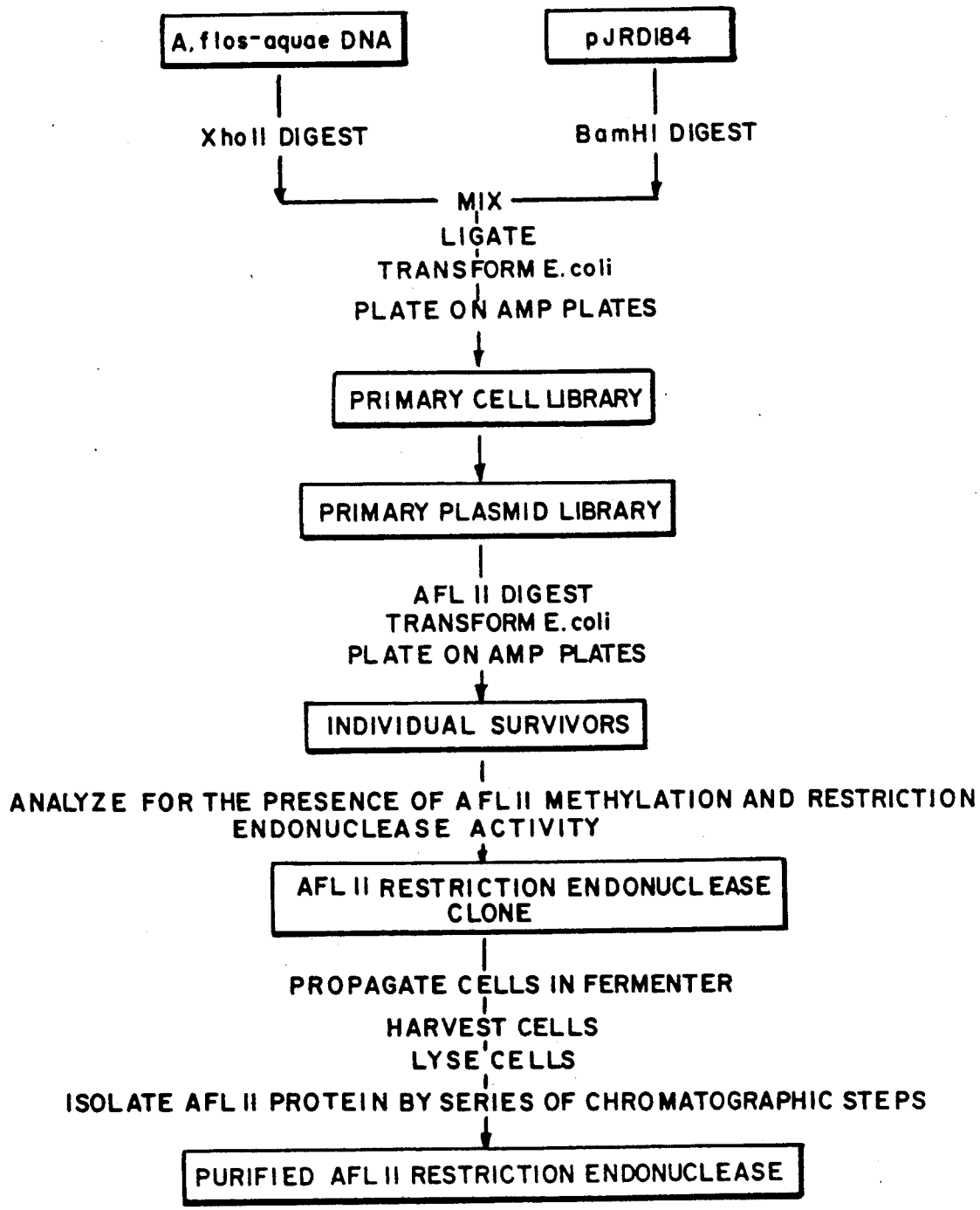
FIG. 1 illustrates the scheme for cloning and producing the Afl II restriction endonuclease.

The method described herein by which the Afl II restriction gene and methylase gene are preferably cloned and expressed are illustrated in FIG. 1, and they include the following steps:

1. The DNA of *Anabaena flos-aquae* is purified. *Anabaena flos-aquae* has been described in a number of publications including Whitehead and Brown, supra, the disclosure of which is hereby incorporated by reference. Samples of this algae are available from the Cambridge Collection of Algae and Protozoa, Cambridge, England under Accession No. CCAP 1403/13f and is also available from Cambio Corporation of Cambridge, England.

2. The DNA is digested partially with the restriction endonuclease Xho II.

3. The digested DNA is ligated to a cloning vector, such as a pBR322 derivative containing an Afl II site. One such preferred vector is pJRD184 obtained from Labofina S. A. of Feluy, Belgium. The resulting mixture is used to transform an appropriate host such as *E. coli* RRl cells.

4. The DNA/cell mixture is plated on antibiotic media selective for transformed cells, such as ampicillin. After incubation, the transformed cell colonies are collected together into a single culture, the primary cell library.

5. The recombinant plasmids are purified in toto from the primary cell library to make a primary plasmid library.

6. The plasmid library is then digested to completion in vitro with the Afl II restriction endonuclease, which was prepared from *Anabaena flos-aquae* cells by a method substantially similar to the method described in Whitehead and Brown, supra. except that: i) the first sepharose 4B chromatography step was omitted; ii) the DEAE chromatography step was omitted; and iii) a mono Q-FPLC chromatography step was included after the heparin-sepharose chromatography step. Afl II restriction endonuclease digestion causes the selective destruction of unmodified, non-methylase-containing, clones, resulting in an increase in the relative frequency of Afl II methylase-carrying clones. Exonuclease and/or phosphatase may also be added to the digestion to enhance the destruction of non-methylase clones.

7. The digested plasmid library DNA is transformed back into a convenient host such as *E. coli* strain RRl, and transformed colonies are again obtained by plating on antibiotic plates. The colonies are picked and their DNA is analyzed for the presence of the Afl II modification gene in the following manner: The plasmid DNA that they carry is purified and incubated in vitro with Afl II restriction endonuclease to determine whether it is resistant to digestion by Afl II. The total cellular DNA (chromosomal and plasmid) of the clone is also purified and incubated with Afl II restriction endonuclease. The DNA of clones that carry the Afl II methylase gene should be fully modified, and both the plasmid DNA and the total DNA should be found to be substantially, or completely resistant to digestion.

9. Clones carrying the Afl II restriction endonuclease are identified by preparing crude extracts of those clones identified in step 8 as carrying the Afl II methylase gene, and assaying the extracts for Afl II restriction endonuclease activity.

10. The Afl II restriction endonuclease may be produced from clones carrying the Afl II restriction and modification genes by propagation in a fermenter in a rich medium containing ampicillin. The cells are thereafter harvested by centrifugation and disrupted by sonication to produce a crude cell extract containing the Afl II restriction endonuclease activity.

11. The crude cell extract containing the Afl II restriction endonuclease activity is purified by standard protein purification techniques such as affinity-chromatography, or ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE I

Cloning of Afl II Restriction Endonuclease Gene

1. DNA purification: To prepare the DNA of *Anabaena flos-aquae* CCAP1403/13f, 1 gm of cell paste was resuspended in 5 ml of 0.1 M Tris-HCl , 0.1 M EDTA pH 7.6. The suspension was divided into two 2.5 ml portions. 3.5 ml of 1.7 mg/ml lysozyme in 0.1 M Tris-HCl, 0.1 M EDTA pH 7.6 was added to each portion and each was incubated for 15 minutes at 37° C. SDS was added to 1%, and proteinase K was added to 0.13 mg/ml and then the portions were incubated for 1 hour at 37° C. 0.4 ml of a solution of 10% SDS and 8% sarcosyl was added to each and incubation was continued at 55° C. for 2 hours. The two portions were then combined and dialysed against four changes of DNA buffer (10 mM Tris-HCl, 1 mM EDTA pH 8.0) for 24 hours. After the first dialysis, the DNA solution was centrifuged at 17,000 rpm for 10 minutes to remove solid debris. The clarified supernatant was returned to dialysis tubing and dialysis was continued. The dialysed DNA solution was then prepared for cesium chloride-ethidium bromide equilibrium density centrifugation by increasing the volume to 40 ml with DNA buffer, and then dividing the DNA solution into two 20 ml portions, to each of which 20 grams of cesium chloride and 0.2 ml of 5 mg/ml ethidium bromide were added. The DNA solution was centrifuged at 44,000 rpm for 48 hours and the resulting band of DNA was removed with a syringe and an 18 gauge needle. The ethidium bromide was removed by extracting 4 times with an equal volume of ice-cold, water-saturated N-butanol. The cesium chloride was removed by dialysis. The DNA was then precipitated with isopropyl alcohol and then redissolved in DNA buffer to a final concentration of approximately 100 ug/ml.

2. Partial digestion: The purified DNA was cleaved with Xho II to achieve partial digestion as follows: 0.3 ml of DNA at 80 ug/ml in 10 mM Tris pH 7.5, 10 mM MgCl$_2$, 50 mM NaCl, 10 mM mercaptoethanol buffer was divided into one 100 ul aliquot and four, 50 ul aliquots. To the 100 ul tube was added 6.4 units of Xho II to achieve 0.8 units of enzyme per ug of DNA. 50 ul was withdrawn from the first tube and transferred to the second tube to achieve 0.4 units Xho II/ug, and so on, each succeeding tube receiving half of the previous amount of Xho II. The tubes were incubated at 37° C. for one hour, then heat-treated at 72° C. for 15 minutes and 10 ul from each was analyzed by agarose gel electrophoresis. Tubes exhibiting moderate, but incomplete digestion were chosen as the source of partial digest fragments for cloning. (These were the 0.4 u/ug, 0.2 u/ug and 0.1 u/ug tubes. The three solutions were mixed together and used as described below.)

3. Ligation: The fragmented DNA was ligated to pJRD184 as follows: 4.0 ug of Xho II - partially digested *A. flos-aquae* DNA (60 ul) was mixed with 2.0 ug of BamH I-cleaved and dephosphorylated pJRD184 (2.5 ul). 10 ul of 10×ligation mix (500 mM Tris, pH 7.5, 100 mM MgCl$_2$, 100 mM DTT, 5 mM ATP) was added, plus 27.5 ul of sterile distilled water to bring the final volume to 100 ul. 3.75 ul of T4 DNA ligase was added and the mixture was incubated at 17° C. for 4 hours then sterilized by the addition of 10 ul of chloroform. Approximately 80 ul of the ligated DNA was used to transfom *E. coli* strain RR1 as follows: The DNA was mixed with 1.0 ml of SSC/CaCl$_2$ (50 mM NaCl, 5 mM Na$_3$ Citrate, 67 mM CaCl$_2$) on ice and 2.0 ml of ice-cold competent *E. coli* RR1 (hsd R−M−, ATCC No. 31343) cells were added. After a 6-minute incubation at 43° C., the cells were diluted by the addition of 8 ml of Luria-broth (L-broth) then incubated at 37° C. for 4 hours.

4. Primary Cell Library: The transformed cell culture was briefly centrifuged, the supernatant was discarded and the cells were resuspended in 1.0 ml of L-broth. 200 ul portions were plated onto Luria-agar (L-agar) plates containing 100 ug/ml ampicillin. After overnight incubation at 37° C., the plates were each flooded with 2.5 ml of 10 mM Tris, pH 7.5, 10 mM MgCl2 and the transformed colonies were scraped together and pooled to form the primary cell library.

5. Primary Plasmid Library: The primary plasmid library was prepared as follows: 2.5 ml of the primary cell library was inoculated into 500 ml of L-broth containing 100 ug/ml ampicillin. The culture was shaken overnight at 37° C. then centrifuged at 4000 rpm for 5 minutes. The supernatant was discarded and the cell pellet was resuspended in 10 ml of 25% sucrose, 50 mM Tris, pH 8.0, at room temperature. 5ml of 0.25M EDTA, pH 8.0, was added, followed by 3 ml of 10 mg/ml lysozyme in 0.25M Tris, pH 8.0. The solution was left on ice for 1 hour, then 12 ml of lytic mix (1% Triton X-100, 50 mM Tris, pH 8.0, 67 mM EDTA) was forcefully pipetted in, and the cell suspension gently swirled to achieve lysis. After lysis, the mixture was transferred to a 50 ml plastic centrifuge tube and spun at 17000 rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1mM EDTA, 100 mM NaCl) was added to the mixture. The solution was transferred to two ⅝ in.×3 in. polyallomer centrifuge tubes and sealed. These tubes were then spun in a Beckman Ti70 rotor for 42 hours at 44000 rpm, 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-Butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was spun at 15000 rpm, 0° C. for 15 minutes and the supernatant discarded. The tube was left on the bench to air-dry for 15 minutes, then the DNA pellet was dissolved in 500 ul of DNA buffer and stored at −20° C. The DNA concentration of plasmids prepared in this way were found to be 100 to 200 ug/ml.

6. Digestion of Plasmid Pool: The primary plasmid pool was digested to destroy non-Afl II methylase clones as follows: The plasmid DNA was diluted to 30 ug/ml in 10 mM Tris pH 7.5, 10 mM MgCl$_2$, 10 mM mercaptoethanol, 50 mM NaCl. A total of 600 ul was prepared and dispensed into 3 tubes, the first containing 300 ul, the other two tubes containing 150 ul each. Afl II was added to the first tube to achieve 8 units/ug DNA, and 150 ul of the resulting solution was transferred to the second tube to achieve 4 units/ug DNA. The third tube received no Afl II. The tubes were incubated at 37° C. for 2 hour. The reactions were inactivated by heating to 72° C. for 10 minutes. 100 ul of each of the reaction mixtures was withdrawn and the DNA was precipitated by the addition of isopropanol. The precipitated DNA was collected by centrifugation and resuspended in 20 ul of DNA buffer (pH 9.0) to achieve approximately 150 ug DNA per ml. 0.4 units of bacterial alkaline phosphatase was added to each tube and each was incubated at 68 degrees for two hours, under paraffin oil. 80 ul of DNA buffer was added, mixed and removed. To this mixture 8 ul of chloroform was added and emulsified by vigorous mixing, and then separated by centrifugation.

7. Transformation: A 12.5 ul sample from each tube was used to transform *E. coli* RR1. The cell/DNA mixtures were plated onto L-agar plates containing 100 ug/ml ampicillin immediately after the heat step, without intermediate dilution and growth. After overnight incubation at 37° C., the plates were examined. Digestion of the plasmid library with Afl II and bacterial alkaline phosphatase was found to have reduced the number of transformants by a factor of about 10$^3$ Approximately 30 individual colonies were picked from the plates that had suffered the greatest attrition (8 units Afl II/ug) Each colony was inoculated into 10 ml of L-broth containing ampicillin, to prepare a miniculture, and was also streaked onto L-agar plates containing ampicillin to prepare a master stock.

8. Analysis of surviving individuals: Approximately 30 of the surviving colonies obtained from section 7 were grown up into 10 ml cultures (section 7) and the plasmids that they carried were prepared by the following miniprep purification procedure, adapted from the method of Birnboinn and Doly (*Nucleic Acids Res.* 7: 1513 (1979)).

Minioreo Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8 0, containing 1 mg/ml lysozyme. After 10 minutes at room temperature, 2.0 ml of 0.2 M NaOH, 1% SDS was added to each tube and the tubes were shaken to lyse the cells, then placed on ice. Once the solutions had cleared, 1.5 ml of 3 M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes. Once dry, the pellets were resuspended in 850 ul of 10 mM Tris, lmM EDTA, pH 8.0. 75 ul of 5 M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris, lmM EDTA, pH 8.0, containing 100 ug/ml RNase and incubated for 1 hour at 37° C. to digest the RNA. The DNA was precipitated once more by the addition of 50 ul of 5 M NaCl followed by 350 ul of isopropanol. After 10 minutes at room temperature, the DNA was spun down by centrifugation for 45 seconds, the supernatants were discarded and the pellets were redissolved in a final solution of 150 ul of 10 mM Tris 1 mM EDTA, pH 8.0. The plasmid minipreps were subsequently analyzed by digestion with Afl II.

Figure 2:
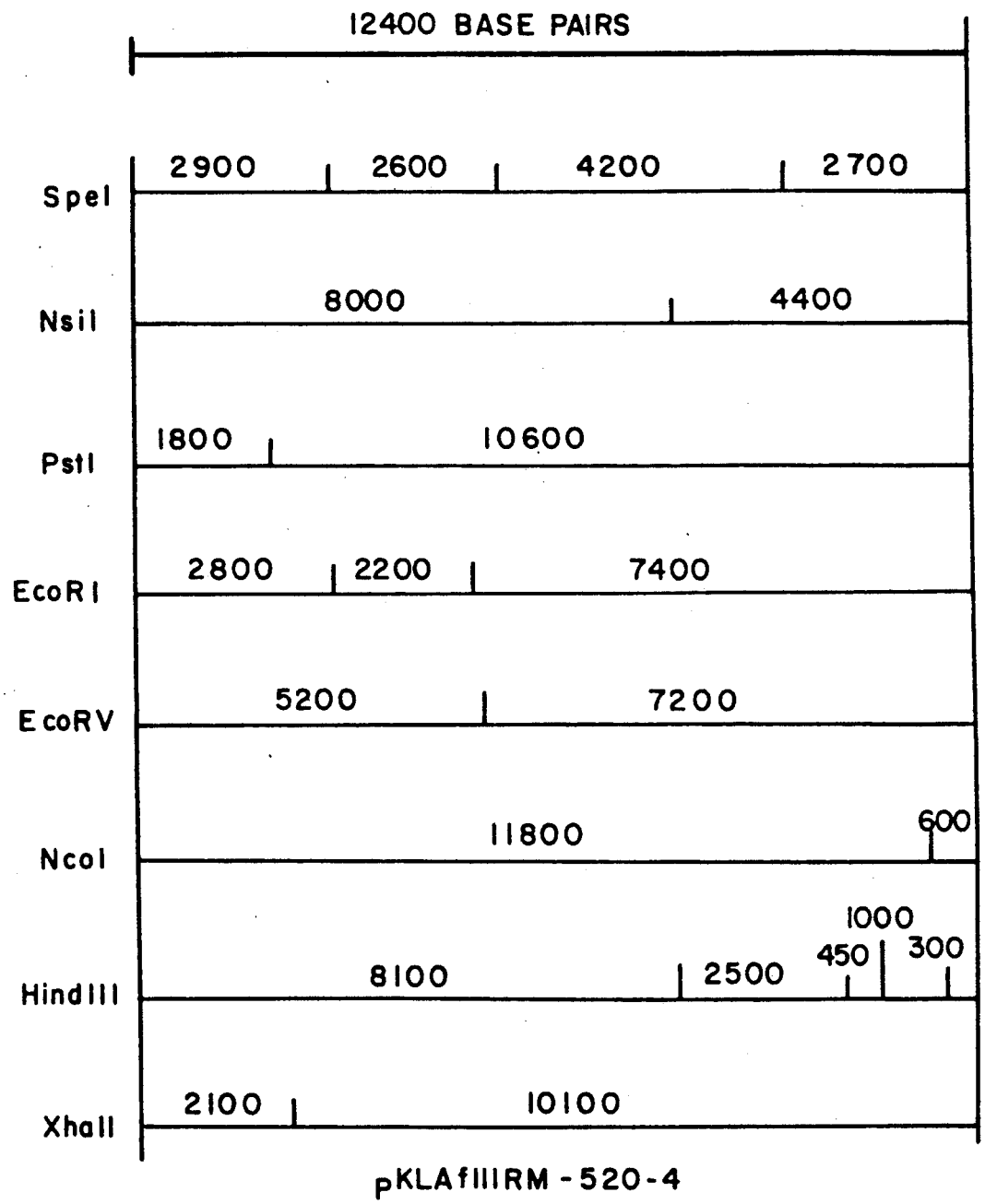
FIG. 2 is a restriction map of a 12.4 Kb Xho II fragment insert encoding the Afl II restriction endonuclease and modification methylase.

9. Methylase Gene Clones: The majority of the plasmids that were analyzed were found to be sensitive to digestion by Afl II and to carry random Xho II fragments of *Anabaena flos-aquae* DNA. These plasmids were spurious survivors, of no further interest, and were discarded. One plasmid was found to be resistant to Afl II and to carry at least two Xho II fragments of approximately 10.1 Kb, 2.1 Kb in length. (See FIG. 2). This plasmid was subsequently shown to carry not only the Afl II modification methylase gene but also restriction endonuclease gene.

10. Restriction Gene Clone: The clone identified above (section 9) as carrying the Afl II modification methylase gene was also found to carry the Afl II restriction endonuclease gene. This was established by in vitro restriction endonuclease assays performed as follows:

Endonuclease Assays: To assay for endonuclease activity, two solutions were prepared:

(i) 10X restriction endonuclease buffer: 100 mM Tris, pH 7.5, 100 mM MgCl$_2$, 100 mM 2-mercaptoethanol, 500 mM NaCl; and (ii) digestion reaction mix: 45 ul lambda-Hind III digested DNA (630ug/ml), 56 ul 10X restriction endonuclease buffer, 459 ul distilled water to achieve 50ug/ml DNA.

Figure 3:
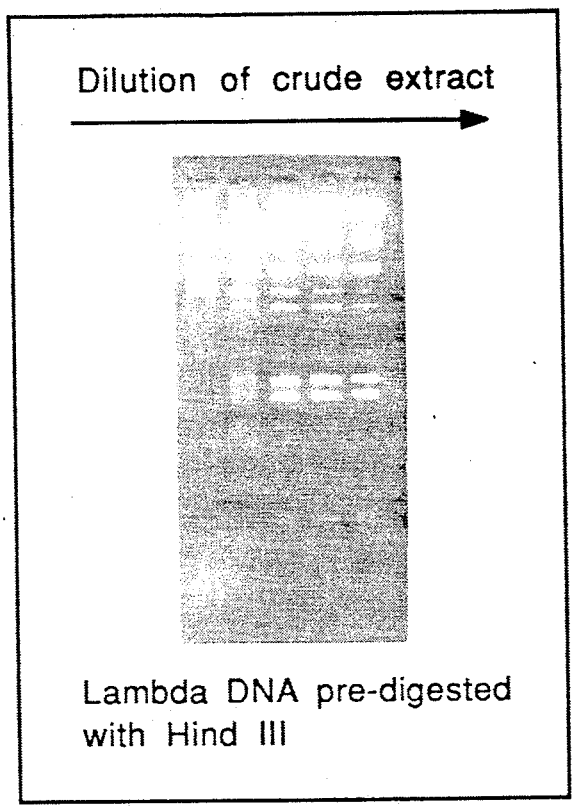
FIG. 3 is a photograph of an agarose gel illustrating Afl II restriction endonuclease activity obtained from the crude extract of pKL AflIIRM 520-4.

The cell extract was prepared as follows: A 100 ml culture of the clone to be tested was grown overnight in L-broth plus 100 ug/ml ampicillin at 37° C. and the cells were pelleted by centrifugation at 4000 rpm for 5 minutes. The supernatant was discarded and the pellet was resuspended in 3 ml of sonication buffer (25 mM KPO$_4$ pH7.5, 10 mM BME, 0.1 mM EDTA). Once resuspended, 0.3 ml of sonication buffer containing 10 mg/ml lysozyme was added. The suspension was swirled and left on ice for 1 hour. A 1 ml sample was transferred to an Eppendorf tube and sonicated gently for three 10-second bursts to disrupt the cells. The tube was spun for 5 minutes in a microfuge and the supernatant was used as the cell extract. To assay the extract, the digestion reaction mix was dispensed into 5 tubes, 150 ul into the first tube and 02.5 ul into each of the remaining 4 tubes. 7.5 ul of the extract was added to the first tube and mixed. 7.5 ul was removed from the first tube and transferred to the second tube, mixed and so on. The first tube thus received 1 ul of extract per ug of DNA, the second tube 0.3 ul/ug, the third tube, 0.1 ul/ug and so on. The tubes, each now containing 100 ul, were incubated at 37° C. for one hour, then a 20 ul sample of each was analyzed by gel electrophoresis. The titre of the extract was found to be approximately 2×10$^4$ units per ml, which corresponds to about 1×10⁵ units of Afl II restriction endonuclease per gram of wet cell paste. (See FIG. 3)

11. The recombinant plasmid pKL AflIIRM 520-4 which carries the genes encoding the Afl II restriction endonuclease and methylase was transferred to *E. coli* strain MM294 (hsd R⁻M⁺, ATCC No. 33625) by transformation to provide transformant *E. coli* MM294 (pKLAfl II-RM520-4), a sample of which has been deposited at the American Type Culture Collection under ATCC Accession No. 40883.

EXAMPLE II

Alf II from *E. coli* MM294(oKLAfl II-520-4)

1. *E. coli* MM294(pKLAfl II-RM520-4) was propagated in a fermenter at 37° C. in L Broth medium consisting of: 10 grams per liter, casein hydrolysate; 5 grams per liter yeast extract; 10 grams per liter NaCl; 1 gram per liter magnesium chloride-hexahydrate; 1 gram per liter glucose; 100 mg per liter ampicillin. The pH was adjusted to 7.2 with NaOH. The cells were collected by centrifugation and the cell paste was stored at −70° C. All subsequent steps were carried out at 4° C.

2. 24 gm of frozen cell paste was thawed and the cells were resuspended in 100 ml of sonication buffer (10 mM KP04, 10 mM 2-mercaptoethanol, 0.1 mM EDTA).

3. The cells were disrupted by sonication, to achieve release of approximately 50 mg of soluble protein per ml of suspended cells.

4. The insoluble cell debris was removed by centrifugation at 10,000 rpm for 45 minutes.

5. The supernatant was adjusted to 0.15 M NaCl and applied to a phosphocellulose column (3 cm×18 cm). The column was washed with two column volumes of sonication buffer containing 0.15 M NaCl. A linear gradient of NaCl from 0.15 M to 1.0 M (total volume, 200 ml) was applied to the column and two ml fractions were collected. The fractions were assayed for the presence of Afl II restriction endonuclease activity. The active fractions were pooled and diluted with sonication buffer to reduce the conductivity to that of a solution of 0.15 M NaCl.

6. The active pool was applied to a heparin sepharose column (2cm×12 cm) and washed with two column volumes of sonication buffer containing 0.15 M NaCl. A linear gradient of NaCl from 0.15 M to 1.0 M (total volume 150 ml) was applied to the column and two ml fractions were again collected. The fractions were assayed for the presence of Afl II restriction endonuclease activity. The active fractions were pooled and dialysed against 100 volumes of H buffer (50 mM KCl; 20 mM Tris-HCl, pH 8.0; 10 mM 2-mercaptoethanol.

7. The dialysate was applied to a 1 ml Mono-Q FPLC column (Pharmacia) and washed with H buffer. A 40 ml linear gradient from 50 mM KCl to 0.6 M KCl in H buffer was applied to the column and one ml fractions were collected. The fractions were assayed for the presence of Afl II restriction endonuclease activity. The two most active fractions are pooled, and two ml of glycerin and 800 ug of bovine serum albumin were added. The purified preparation was stored at −20° C.

What is claimed is:

1. Isolated DNA coding for the AflII restriction endonuclease, wherein the isolated DNA is obtainable from the vector pKLAflII-RM520-4.

2. A recombinant DNA vector comprising a vector into which a DNA segment coding for the AflII endonuclease has been inserted.

3. Isolated DNA coding for the AflII restriction endonuclease and methylase, wherein the isolated DNA is obtainable from the vector pKLAflII-RM520-4.

4. A cloning vector which comprises the isolated DNA of claim 3.

5. The cloning vector of claim 4, wherein the cloning vector comprises pKLAflII-RM520-4.

6. A host cell transformed by the vector of claim 2, 4 or 5.

7. A method of producing an AflII restriction endonuclease comprising culturing a host cell transformed with the vector of claim 2, 4 or 5 under conditions suitable for the expression of said endonuclease.

8. A method of cloning DNA coding for an AflII restriction endonuclease comprising:
a) purifying DNA from *Anabaena flos-aquae*;
b) digesting the purified DNA with XhoII to form DNA fragments;
c) ligating the DNA fragments into a cloning vector containing at least one AflII recognition site or its equivalent;
d) transforming a host cell with the cloning vector of step c) to form a cell library;
e) purifying recombinant vectors from the cell library to form a plasmid library;
f) contacting the plasmid library of step e) with AflII to form a digestion pool, transforming the digestion pool into a host cell, and screening for the presence of one or more cloning vectors containing DNA coding for an AflII methylase;
g) screening the cloning vectors of step f) which contain DNA coding for AflII methylase for the presence of DNA coding for an AflII restriction endonuclease, and
h) isolating the cloning vectors of step g) which contain DNA coding for AflII restriction endonuclease.

9. The method of claim 8, wherein the cloning vector of step c) is pJRD184.

10. A method for producing AflII restriction endonuclease comprising:
a) purifying DNA from *Anabaena flos-aquae*;
b) digesting the purified DNA with XhoII to form DNA fragments;
c) ligating the DNA fragments into a cloning vector containing at least one AflII recognition site or its equivalent;
d) transforming a host cell with the cloning vector of step c) to form a cell library;
e) purifying recombinant vectors from the cell library to form a plasmid library;
f) contacting the plasmid library of step e) with AflII to form a digestion pool, transforming the digestion pool into a host cell, and screening for the presence of one or more cloning vectors containing DNA coding for an AflII methylase;
g) screening the cloning vector of step f) which contains DNA coding for AflII methylase for the presence of DNA coding for an AflII restriction endonuclease;
h) isolating the cloning vector of step g) which contains DNA coding for AflII restriction endonuclease; and
i) culturing a host cell transformed with the cloning vector of step h) under conditions suitable for expression of AflII restriction endonuclease.

11. The method of claim 10, wherein the cloning vector of step c) is pJRD184.

* * * * *

UNITED STATES PATENT AND TRADEMARK OFFICE
CERTIFICATE OF CORRECTION

PATENT NO. : 5,030,569

DATED : July 9, 1991

INVENTOR(S) : Keith Lunnen & Geoffrey Wilson

It is certified that error appears in the above—identified patent and that said Letters Patent is hereby corrected as shown below:

Col. 7, line 50, "Birnboinn" should be --Birnboim--.
Col. 7, line 52, "Minioreo" should be --Miniprep--.
Col. 8, line 59, "02.5" should be --102.5--.
Col. 9, line 13, "Alf II" should be --Afl II--.
Col. 9, line 13, "oKLAfl II-520-4" should be --pKLAfl II-520-4--.

Signed and Sealed this

Tenth Day of November, 1992

Attest:

DOUGLAS B. COMER

Attesting Officer

Acting Commissioner of Patents and Trademarks